United States Patent [19]

Middle et al.

[11] Patent Number: 5,484,060
[45] Date of Patent: Jan. 16, 1996

[54] STERILE INFANT IDENTIFICATION DEVICE

[76] Inventors: George H. Middle, 1300 Clough Rd., Reno, Nev. 89509; William D. Glennon, 14115 Moonrise Ct., Reno, Nev. 89502

[21] Appl. No.: 386,288

[22] Filed: Feb. 9, 1995

[51] Int. Cl.$^6$ .......................... A61B 17/06; B65D 85/00
[52] U.S. Cl. .......................... 206/438; 206/459.5; 40/324
[58] Field of Search .......................... 206/438, 459.5, 206/439, 564; 40/324

[56] References Cited

U.S. PATENT DOCUMENTS

| | | |
|---|---|---|
| D. 305,151 | 12/1989 | Bisha . |
| 2,889,848 | 6/1959 | Redmer . |
| 3,316,935 | 5/1967 | Kaiser . |
| 3,938,686 | 2/1976 | Milligan et al. .................. 206/459.5 X |
| 4,137,940 | 2/1979 | Faisandier . |
| 4,155,362 | 5/1979 | Jess . |
| 4,402,407 | 9/1983 | Maly ........................................... 206/438 |
| 4,439,179 | 3/1984 | Lueders . |
| 4,444,310 | 4/1984 | Odell ........................................ 206/366 |
| 4,474,016 | 10/1984 | Winchell .............................. 206/438 X |
| 4,689,043 | 8/1987 | Bisha . |
| 4,750,619 | 6/1988 | Cohen et al. ........................... 206/438 |
| 4,856,517 | 8/1989 | Collins . |
| 5,117,981 | 6/1992 | Crawford et al. ...................... 206/570 |
| 5,281,228 | 1/1994 | Wolfson . |

*Primary Examiner*—Paul T. Sewell
*Assistant Examiner*—Tara L. Laster
*Attorney, Agent, or Firm*—Nydegger & Associates

[57] ABSTRACT

An infant identification device includes a clamp and a clamp container for holding the clamp. The container is supplied with the clamp sealed in sterile conditions under a cover. The clamp has a label area and the cover includes a region of pressure transferable ink. When the clamp is sealed in the container the region of pressure transferable ink lies over the label area of the clamp. Thus, writing applied to the cover over the pressure transferable ink is transferred to the label area of the clamp. Once the clamp has been inscribed, it may be removed from the container by peeling back the cover. After removal, the clamp is applied to the umbilical cord of the infant thereby providing a sealing means for the cord and a means of positive identification for the infant.

19 Claims, 2 Drawing Sheets

STERILE INFANT IDENTIFICATION DEVICE

FIELD OF THE INVENTION

The present invention pertains generally to identification tags for newborn infants. More particularly, the present invention pertains to systems which maintain the sterility of an infant identification tag thereby reducing the risk of infection after the tag is applied. The present invention is particularly, but not exclusively, useful as a system for transferring an identifier onto a clamp under sterile conditions for subsequent attachment of the clamp to the umbilical cord of an infant.

BACKGROUND OF THE INVENTION

Misidentification of newborn infants, whether intentional or inadvertent, is a source of great concern, both for medical care providers as well as the effected families. As a result, several methods of infant identification have been developed. For instance, the use of identification bracelets, generally applied to the arm or leg of an infant, is well known. These bracelets carry a paper or plastic label upon which identifying information may be written. Once placed around the ankle or wrist, the written label becomes a means whereby hospital staff or other attendants may correctly identify each infant. In practice, however, these bracelets must be loosely applied to avoid possible damage to the infant's circulation or skin. As a result, it is always possible that a particular bracelet will become dislodged or lost thereby increasing the chance for misidentification.

Another problem associated with traditional infant identification bracelets is the possibility of disease transmission. More specifically, the application of written or printed information to traditional infant identification bracelets has generally involved some degree of manual manipulation of the bracelet. Maintenance of the sterility of the bracelet, therefore, has been dependent on the use of rubber gloves or other anti-microbial measures. In cases where these measures have been overlooked or purposely avoided, the sterility of the bracelet may have been compromised. The possibility of bracelet borne infection is especially serious in cases where infants are born prematurely with potentially weakened immunological systems.

In light of the above, it is an object of the present invention to provide an infant identification device that allows infants to be quickly and positively identified. It is another object of the present invention to provide an infant identification device which will remain attached to the infant during normal use. Yet another object of the present invention is to provide an infant identification device that protects the sterility of the device as the device is inscribed with identifying information. Still another object of the present invention is to provide an infant identification device which is removable with minimal risk to the infant. Still another object of the present invention is to provide an infant identification device which is relatively simple to use, is relatively easy to implement and is comparatively cost effective.

SUMMARY OF THE PREFERRED EMBODIMENTS

The present invention provides an umbilical clamp and a clamp container. Together, the clamp and the container provide a system allowing the clamp to be inscribed with identifying information without compromising the sterility of the clamp. The clamp may then be applied to the umbilical cord of an infant, sealing the cord and providing a secure means of identification for the infant.

In greater detail, the present invention includes a hinged, locking clamp designed to be fastened around the umbilical cord of an infant at the time of the infant's birth. After the clamp is fastened, the umbilical cord is sealed and may be trimmed to remove the excess portion.

Included on the clamp is a label area upon which writing or printing may be displayed. By inscribing a unique marking, such as the name of the infant, on the label area, a positive means of identification may be securely fastened to the infant. In general, the clamp is intended to remain attached to the umbilical cord until the cord naturally separates from the infant. In cases where earlier removal is desired, the clamp is designed to be removable by cutting the hinge.

To provide a sterile means for applying the unique markings to the label area, the clamp is sealed into a clamp container. The container includes a tray with a recess into which the clamp is placed. The tray is then covered with a peel-off cover holding the clamp inside. The interior surface of the cover, which faces the clamp, includes a region positioned over the label area of the clamp upon which a pressure transferable ink is deposited. Writing applied to the cover causes the ink deposited on the region to migrate to the clamp thereby inscribing the clamp with a copy of the writing applied to the cover. In this fashion, the name of the infant, or other unique marking, may be applied to the clamp without removing the clamp from the container thereby protecting the sterility of the clamp. For the purposes of the present invention, a smear and water resistant ink is chosen for use as the pressure transferable ink thereby insuring that the writing applied to the clamp remains legible as the infant is washed or otherwise handled.

Once the process of inscribing the clamp is complete, the peel-off cover may be removed from the tray, allowing the clamp to be removed from the recess. After removal, the clamp is affixed over the umbilical cord of the infant and used to seal the cord. The label on the clamp provides a means by which the infant may be identified until the clamp is removed either by cutting the hinge or by the eventual separation of the umbilical cord from the infant.

DESCRIPTION OF THE PREFERRED EMBODIMENT

Figure 1:
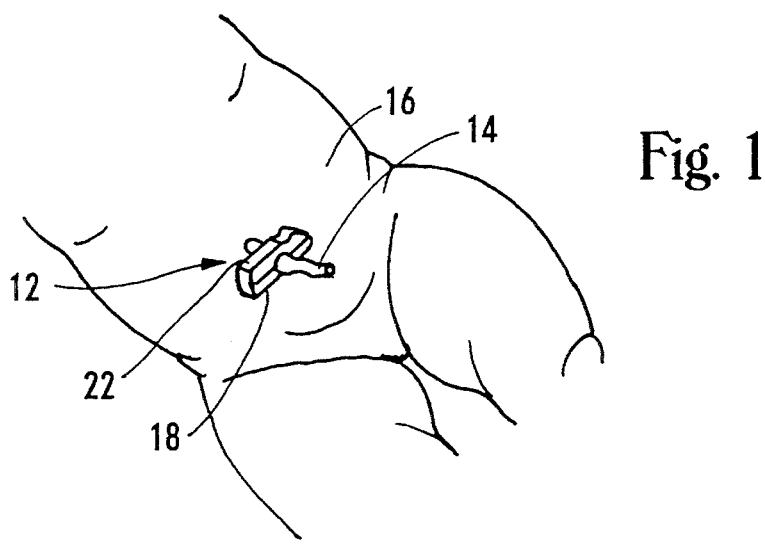
FIG. 1 is a perspective view of the clamp of the present invention operationally placed around the umbilical cord of an infant.

The present invention provides an umbilical clamp and a clamp container. Together, the clamp and the clamp container provide a device and a system whereby the sterility of the clamp is protected as the clamp is inscribed with identifying information. Once inscribed, the sterile identification tag may be affixed to an infant. The intended environment for the present invention may be seen generally in FIG. 1 where a clamp 12 is shown affixed around the umbilical cord 14 of an infant 16.

Figure 2:
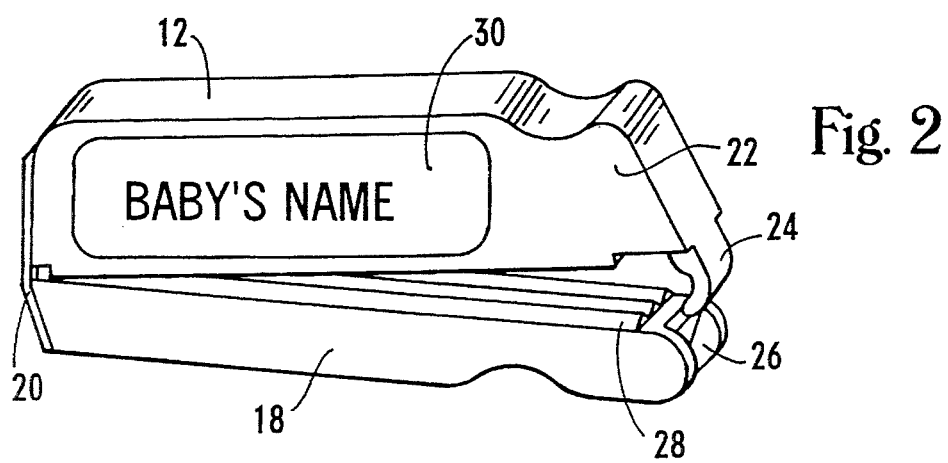
FIG. 2 is an isometric view of the clamp of the present invention.

The structural details of the clamp 12 may, perhaps, be better appreciated by reference to FIG. 2 where it will be seen that the clamp 12 includes a base 18 which is attached by a living hinge 20 to a clasp 22. FIG. 2 also shows that the clasp 22 includes a hook 24 and that the hook 24 is positioned to engage a hook retainer 26 included in the base 18. Operationally, the hinge 20 allows the clasp 22 to move between an open configuration where the clasp 22 is ajar and a closed configuration where the clasp 22 lies along the base 18. Additionally, as the clasp 22 adopts the closed configuration, the hook 24 engages the hook retainer 26 locking the clasp 22 into the closed configuration. Once the clamp 12 has been placed into the closed configuration, the hook 24 and hook retainer 26 hold the clamp 12 in the closed configuration until the clasp 22 is removed from the base 18 by cutting the hinge 20. Preferably, the base 18, hinge 20 and clasp 22 are formed from a single piece of plastic.

Functionally, it may be appreciated that clamp 12 is intended to be positioned with the base 18 and clasp 22 on opposite sides of the umbilical cord 14 of the infant 16. When positioned in this manner, a squeezing force is applied to the umbilical cord 14 as the clamp 12 is placed in the closed configuration. The squeezing force seals the umbilical cord 14 and prevents fluid loss from the infant 16. Preferably, the clamp 12 is dimensioned so that it may be closed over the umbilical cord 14 using a single hand with approximately four to six pounds (4–6 lbs.) of pressure. To prevent the clamp 12 from becoming dislodged after application, the base 18 and the clasp 22 include a series of inward facing ridges 28 designed to give the clamp 12 a sure grip on the umbilical cord 14.

To achieve the goals of the present invention, a label area 30 is included on the clasp 22. The label area 30 may be fabricated as a inscribable area molded into the clasp 22 or as a paper surface attached to the clasp 22. Alternatively, the label area 30 may be fabricated as a soft, indentable material such as soft metal. By applying a unique marking to the label area 30, a positive means of identification may be conveniently associated with the infant 16 as the umbilical cord 14 is clamped.

Figure 3:
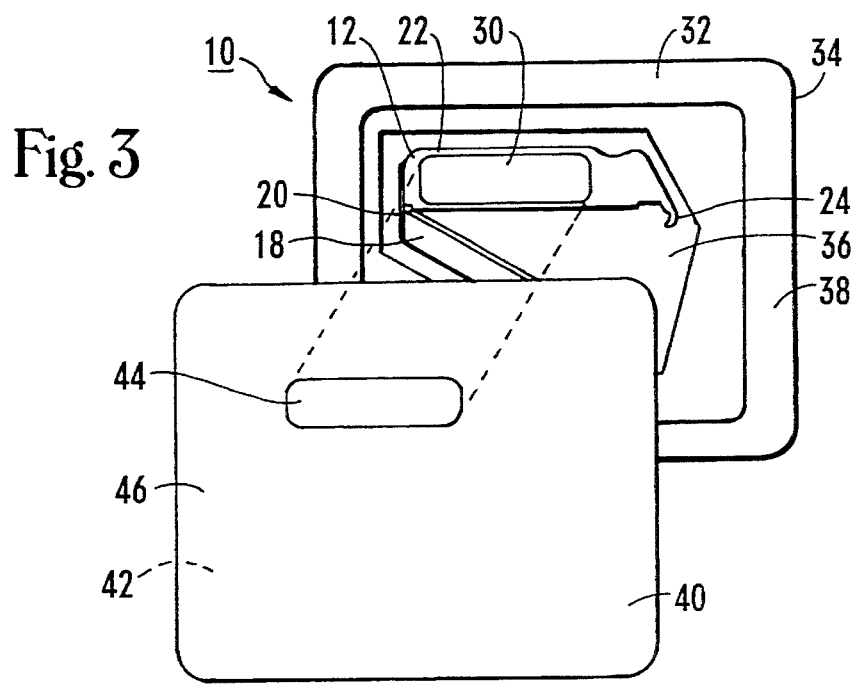
FIG. 3 is a top elevational view of the clamp container of the present invention with the container cover removed to reveal the clamp of the present invention.
Figure 4:
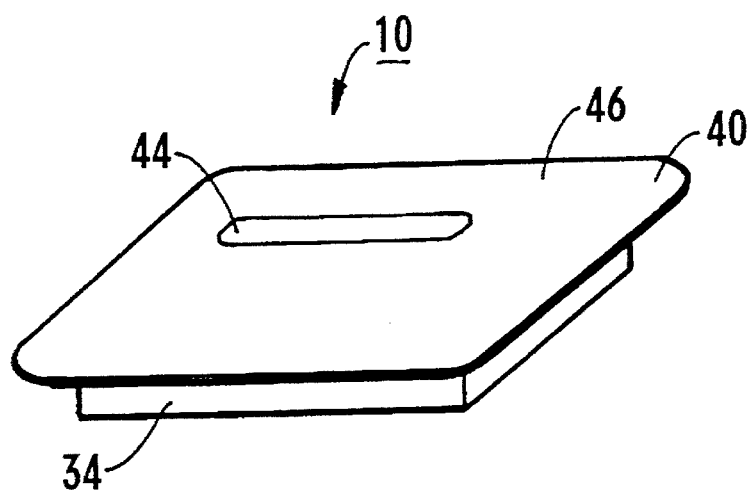
FIG. 4 is an isometric view of the clamp container of the present invention.

The clamp container 32 shown in FIG. 3 provides a sterile means by which a unique marking may be applied to the label area 30. In greater detail, FIG. 3 shows that the clamp container 32 includes a tray 34 formed with a recess 36 shaped to receive the clamp 12. Preferably, the tray 34 is formed as a single piece of plastic or cardboard. At the edge of the tray 34, a flat lip 38 is provided. As shown in FIG. 3, the lip 38 extends around the circumference of the tray 34.

A peel-off cover 40 is affixed with an adhesive to the lip 38 to cover the tray 34 holding the clamp 12 within the recess 36. Preferably, the cover 40 and tray 34 are fabricated from a material which allows for the passage of a toxic sterilizing gas into the recess 36 thereby allowing the clamp 12 to be sterilized while the clamp 12 is positioned in the clamp container 32. Alternatively, the clamp 12 may be sterilized while positioned in the clamp container 32 by exposure to high-energy radiation. The adhesive used to attach the cover 40 to the lip 38 of the tray 34 is of a type which provides a high-strength bond between the cover 40 and the lip 38 of the tray 34 preventing inadvertent detachment of the cover 40 or impairment of the sterility of the clamp 12 until the cover 40 is intentionally peeled back from the tray 34 allowing the clamp 12 to be removed for use.

The interior side 42 of the cover 40, which faces the clamp 12, includes a region 44 upon which a pressure transferable ink is deposited. As shown in FIG. 3, the region 44 is positioned to face and lie over the label area 30 of the clamp 12. It may be appreciated that pressure applied to the exterior side 46 with an instrument, such as a pen (not shown), over the region 44, will cause the ink deposited on the interior side 42 of the cover 40 in the region 44 to migrate to the label area 30. Specifically, writing applied to the exterior side 46, over the region 44, will cause a corresponding inscription to be applied to label area 30. It may also be appreciated that the presence of the cover 40 ensures that the sterility of the clamp 12 is not impaired during the inscription process. Therefor, the material chosen for the cover 40 and the tray 34 must be strong enough to protect the sterility of the clamp 12 during the inscription process. Generally, a material such as Tyvek is appropriate.

For purposes of the present invention, the pressure transferable ink used in region 44 should be non-toxic, smear resistant and relatively indelible thereby ensuring that the inscription applied to the label area 30 remains intelligible during the time that the clamp 12 is in use even as the infant 16 is washed or otherwise handled. Alternatively, the label area 30 may be fabricated from a soft, indentable material, such as soft metal, allowing the label area 30 to be inscribed or indented by applying pressure to the exterior side 46, over the region 44. It may be appreciated that in cases where an indentable material is used for label area 30, the pressure transferable ink may be eliminated from region 44. Additionally, there may be cases where it is desirable to include extra labeling areas in addition to label area 30.

In these cases, additional labeling areas can easily be added to clamp 12 and additional regions like region 44 may be added to the cover 40 or tray 34.

Figure 5:
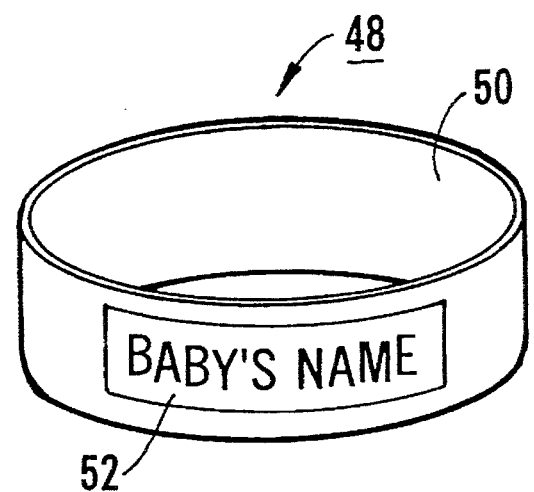
FIG. 5 is an isometric view of an identification bracelet shown as an alternate embodiment for the clamp of the present invention.

It should be appreciated that the particular clamp 12 disclosed herein is intended to be exemplary and that the utility provided by the combination of the clamp 12 and the clamp container 32 is adaptable to varying embodiments. For instance, the clamp container 32 is adaptable for use with the identification bracelet 48 shown in FIG. 5. As seen in that figure, the bracelet 48 includes a band 50 and a label area 52. Like the label area 30 included in the clamp 12, the label area 52 included in the bracelet may be formed as an inscribable area, paper surface or indentable surface. As may be readily appreciated, the tray 34 and particularly the recess 36 may be easily adapted so that the container 32 provides the same combination of enhanced sterility and pressure transferable identification when used with the bracelet 48.

OPERATION

In the use of the infant identification device 10 of the present invention, an identifying marking is first applied to the clamp 12. This process generally involves writing the name of the infant 16 on the region 44 of the cover 40. The writing causes the ink deposited on the interior side 42 of the cover 40 in the region 44 to transfer from the cover 40 to the label area 30 of the clamp 12. Thus the clamp 12 is inscribed with the name of the infant 16. Because the cover 40 protects the sterility of the clamp 12, the inscription process may be performed without the need for sterile precautions such as rubber gloves. In fact, the inscription process may even be performed by the expectant parents.

At the time of birth, the cover 40 is peeled away from the tray 34 allowing the clamp 12 to be removed from the recess 36. The clamp 12 is then applied over the umbilical cord 14 of the infant 16 with the base 18 and clasp 22 on opposite sides of the cord 14. The base 18 and clasp 22 are then squeezed together until the hook 24 engages the hook retainer 26 locking the clamp 12 in the closed configuration with the umbilical cord 14 sealed. Once the clamp 12 is applied, the majority of the umbilical cord 14 may be cut and removed from the infant 16, leaving the clamp 12 attached to a short segment of the umbilical cord 14 which remains attached to the infant 16. After the umbilical cord 14 has been cut, the information inscribed on the label area 30 serves as a means whereby the infant 16 may be positively identified. In general, the clamp 12 will remain attached to the umbilical cord 14 and infant 16 until the cord 14 naturally separates from the infant 16. In cases where removal of the clamp 12 becomes necessary at some earlier time, the clamp 12 may be removed by cutting the hinge 20.

While the infant identification device as herein shown and disclosed in detail is fully capable of obtaining the objects and providing the advantages herein before stated, it is to be understood that they are merely illustrative of the presently preferred embodiments of the invention and that no limitations are intended to the details of construction or design herein shown other than as described in the appended claims.

We claim:

1. An identification device for an infant which comprises:
   a tag having a surface;
   a tray formed with a recess for receiving said tag therein;
   a cover bounded by a periphery, said cover having a first side and a second side with a region on said second side, said periphery on said second side of said cover being affixed to said tray to hold said tag in said recess with said region in juxtaposition with said surface of said tag; and
   a pressure transferable ink deposited on said region of said cover for transferring impressions to said surface of said tag by migration of said pressure transferable ink from said cover to said surface in response to impressions applied to said first side of said cover.

2. An identification device as recited in claim 1 wherein said cover is affixed to said tray with a peel-off adhesive bond.

3. An identification device as recited in claim 1 wherein said cover is a gas permeable material for allowing said identification device to be sterilized by exposure to a toxic gas.

4. An identification device as recited in claim 1 wherein said cover is composed of a material, said material allowing said identification device to be sterilized by exposure to radiation.

5. An identification device as recited in claim 1 wherein said tag is an identification bracelet.

6. An identification device as recited in claim 1 wherein said tag is a clamp attachable to the umbilical cord of an infant.

7. An identification device as recited in claim 6 wherein said clamp further comprises:
   a substantially flat body having a first end and a second end;
   a substantially flat clasp having a first end and a second end;
   a hinge connecting said first end of said body and said first end of said clasp to allow said clasp to move between an open configuration and a closed configuration; and
   a hook attached to said second end of said clasp, said hook engaging said body as said clasp adopts said closed configuration.

8. An identification device as recited in claim 7 wherein said hinge is formed as a living hinge.

9. An identification device for an infant which comprises:
   means for identifying an infant;
   means for receiving said identification means;
   means attachable to said receiving means for holding said identification means in said receiving means to maintain said identifying means in a sterile environment; and
   means for inscribing identifying information on to said identification means when said identification means is held in said receiving means by said retaining means.

10. An identification device as recited in claim 9 wherein said identification means includes a surface.

11. An identification device as recited in claim 10 wherein said receiving means comprises a tray formed with a recess for receiving said identification means therein.

12. An identification device as recited in claim 11 wherein said retaining means comprises a cover bounded by a periphery, said cover having a first side and a second side with a region on said second side, said periphery on said second side of said cover being affixed to said tray to hold said identification means in said recess with said region in juxtaposition with said surface of said identification means.

13. An identification device as recited in claim 12 wherein said printing means comprises a pressure transferable ink deposited on said region of said cover for transferring impressions applied to said first side of said cover to said surface of said identification means by migration of said pressure transferable ink from said cover to said surface.

14. An identification device as recited in claim 12 wherein said surface is pressure indentable for recording impressions applied to said first side of said cover over said surface.

15. An identification device as recited in claim 9 wherein said retaining means is gas permeable allowing said identification device to be sterilized by exposure to a toxic gas.

16. An identification device as recited in claim 9 wherein said retaining means is substantially transparent to radiation allowing said identification device to be sterilized by exposure to radiation.

17. An identification device as recited in claim 9 wherein said identification means is an identification bracelet.

18. An identification device as recited in claim 9 wherein said identification means is a clamp attachable to the umbilical cord of an infant.

19. A method for placing an identifier on a tag having a surface to maintain sterility of said tag for subsequent use which comprises the steps of:
   providing a device which comprises a tray formed with a recess for receiving said tag therein, a cover bounded by a periphery, said cover having a first side and a second side with a region on said second side, said periphery on said second side of said cover being affixed to said tray to hold said tag in said recess with said region in juxtaposition with said surface of said tag, and a pressure transferable ink deposited on said region of said cover for transferring impressions to said surface. of said tag by migration of said pressure transferable ink from said cover to said surface in response to impressions applied to said first side of said cover;
   inscribing an identifier on said first side of said cover of said device over said region;
   detaching said cover from said tray to reveal said tag; and
   removing said tag from said recess of said tray.

* * * * *